(12) United States Patent
Cardelius et al.

(10) Patent No.: US 9,289,569 B2
(45) Date of Patent: Mar. 22, 2016

(54) BREATHING APPARATUS WITH MONITORED DELIVERY DEVICE

(75) Inventors: Erik Cardelius, Solna (SE); Magnus Hallbäck, Danderyd (SE); Pär Emtell, Vällingby (SE); Lars Wallen, Spanga (SE)

(73) Assignee: Maquet Critical Care AB, Solna (SE)

( * ) Notice: Subject to any disclaimer, the term of this patent is extended or adjusted under 35 U.S.C. 154(b) by 962 days.

(21) Appl. No.: 13/510,046

(22) PCT Filed: Nov. 16, 2010

(86) PCT No.: PCT/EP2010/067610
§ 371 (c)(1),
(2), (4) Date: Aug. 30, 2012

(87) PCT Pub. No.: WO2011/058196
PCT Pub. Date: May 19, 2011

(65) Prior Publication Data
US 2012/0312302 A1    Dec. 13, 2012

(30) Foreign Application Priority Data
Nov. 16, 2009  (SE) ...................................... 0950868

(51) Int. Cl.
| A61M 15/00 | (2006.01) |
| A61M 16/10 | (2006.01) |
| A61M 16/12 | (2006.01) |
| A61M 16/18 | (2006.01) |

(52) U.S. Cl.
CPC ............. *A61M 16/104* (2013.01); *A61M 16/12* (2013.01); *A61M 16/18* (2013.01); *A61M 2016/1025* (2013.01); *A61M 2016/1035* (2013.01); *A61M 2202/0208* (2013.01); *A61M 2202/0283* (2013.01); *A61M 2205/18* (2013.01); *A61M 2205/3331* (2013.01); *A61M 2205/3375* (2013.01)

(58) Field of Classification Search
CPC ... A61M 16/104; A61M 16/12; A61M 16/18; A61M 2016/1025; A61M 2016/1035
See application file for complete search history.

(56) References Cited

U.S. PATENT DOCUMENTS

| 5,546,931 A | 8/1996 | Rusz |
| 5,581,014 A * | 12/1996 | Douglas ........................ 73/24.01 |
| 5,701,888 A | 12/1997 | Tham et al. |
| 6,912,907 B2 * | 7/2005 | Fujimoto ........................ 73/597 |
| 2004/0149285 A1 * | 8/2004 | Wallen ..................... 128/204.18 |
| 2007/0203448 A1 | 8/2007 | Melker et al. |

FOREIGN PATENT DOCUMENTS

| EP | 0 545 567 A1 | 6/1993 |
| EP | 1 441 222 A2 | 7/2004 |

(Continued)

*Primary Examiner* — Justine Yu
*Assistant Examiner* — Kathrynn Lyddane
(74) *Attorney, Agent, or Firm* — Schiff Hardin LLP

(57) ABSTRACT

A breathing apparatus has a first delivery device for adding a volume of a substance to a gas flow, the delivery device having a gas inlet and a gas outlet. A unit monitors a presence of the substance in a gas downstream the delivery device using a first sensor unit at the gas outlet that provides a first measurement value based on an acoustic property of a gas in a first conduit. A second sensor unit at the gas inlet provides a second measurement value based on an acoustic property of a gas present in the second conduit. A control unit determines the presence of the substance based on the first measurement value or based on a comparison of the first measurement value and the second measurement value.

22 Claims, 4 Drawing Sheets

(56) References Cited

FOREIGN PATENT DOCUMENTS

| | | |
|---|---|---|
| EP | 2 050 479 A2 | 4/2009 |
| GB | 2 367 360 | 4/2002 |
| GB | 2 367 360 A | 4/2002 |
| WO | WO 99/09388 A2 | 2/1999 |
| WO | 2009/000328 A1 | 12/2008 |
| WO | WO 2009/032540 A2 | 3/2009 |
| WO | 2009/062550 A1 | 5/2009 |

* cited by examiner

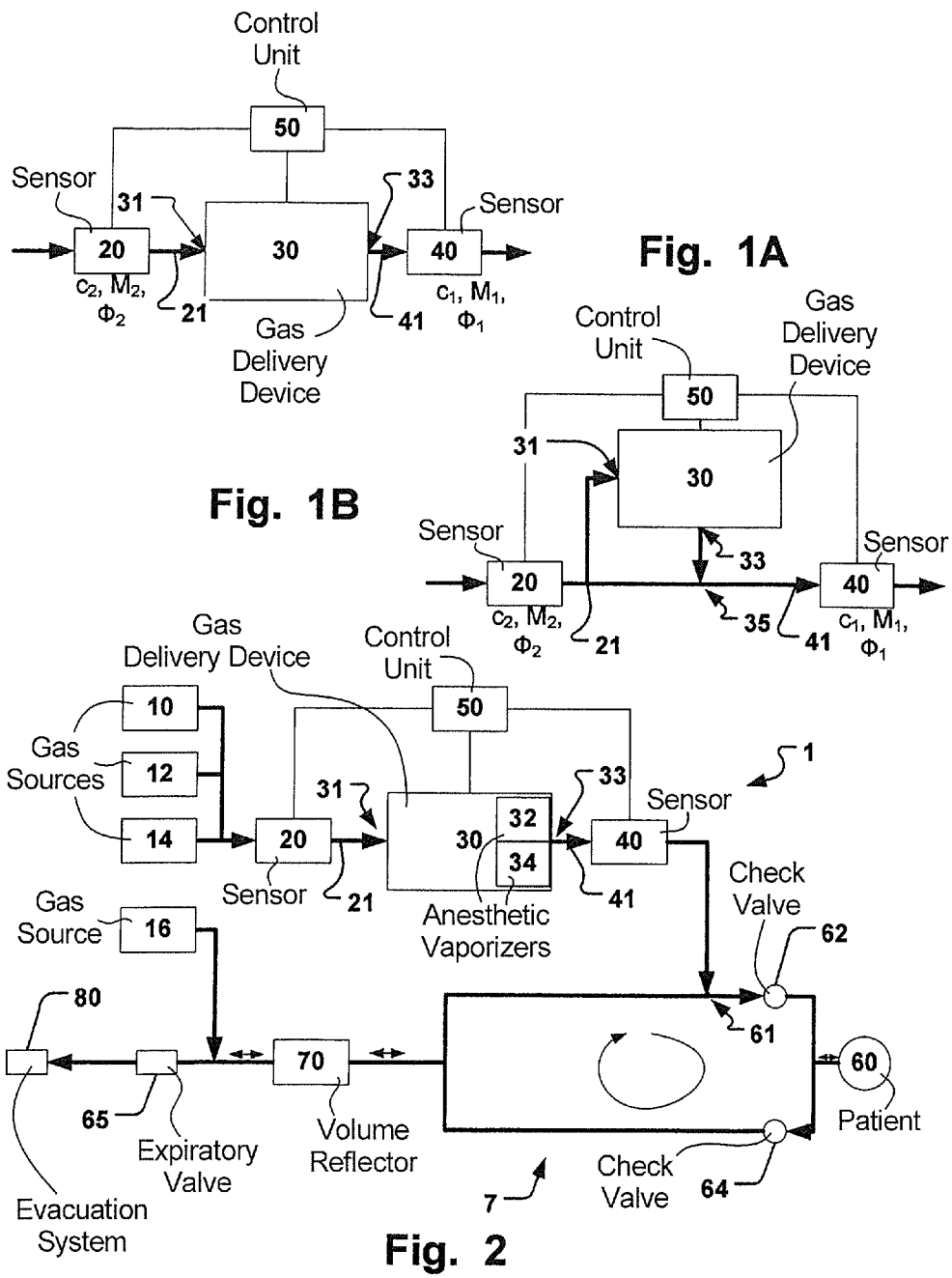

BREATHING APPARATUS WITH MONITORED DELIVERY DEVICE

BACKGROUND OF THE INVENTION

1. Field of the Invention

This invention pertains in general to the field of breathing apparatuses having delivery devices for delivery of substances via a gas flow to a patient. More precisely, the invention relates to monitoring the proper function of such delivery devices for safety purposes.

2. Description of the Prior Art

Various delivery devices for substances to be delivered to patients connected to breathing apparatuses are known, such as anesthetic vaporizers for gasifying liquid anesthetic agents. Breathing apparatuses include for instance anesthesia machines, intensive care ventilators with added anesthesia capabilities, etc.

An erroneous function of such delivery devices may involve a safety hazard potentially exposing a connected patient to situations with dire consequences, e.g. when a non-desired amount of the substance should be delivered to the patient.

Hence, there is a need of controlling the correct or desired function of such delivery devices in the breathing apparatuses.

For instance EP-0545567-A1 discloses a method and apparatus for metering to a patient an anesthetic vaporized from anesthetic liquid held in a liquid space of a liquid container into a gas space. The anesthetic dose contained in a gas flow supplied to a patient is determined by the volume/flow of gas passing through the liquid space, i.e. a traditional by-pass vaporizer. The dose is adjusted in a manner that the dosage of anesthetic in a gas intended to be respired by a patient matches a desired dosage and the dosage adjustment of anesthetic contained in a gas supplied to a patient is effected automatically whenever the current dosage differs from a desired value.

However, the apparatus of EP-0545567-A1 needs to determine a desired dosage of anesthetic. Determining a dosage as described in EP-0545567-A1 may be regarded being complicated. Hence there is a need for a simpler system. Further, the apparatus uses either pressure drop based flow meters, or optical sidestream based measurements systems, which are expensive and have further drawbacks.

When using pressure drop flow sensors or heat wire anemometers for measuring gas flow, compensation has to be made for changes in gas composition.

Optical gas analyzers are good but expensive. Moreover, taking a sidestream gas sample from the mainstream involves a time delay for the measurement due to the transportation time from the sample point to the optical gas analyzer; the main gas flow is interfered with by drawing a sample volume, which itself raises issues where to dispose or feedback the sample gas volume after measurement from the optical analyzer; sampling is only based on a small portion of the gas conduit at the sampling point, amongst other disadvantages.

Furthermore the output of sensor units such as a pressure drop based flow meter or a heat wire based flow meter is depended on both the gas flow and physical properties of the measured gas. Particularly in a fault situation, where it is most important to ensure patient safety can both flow and gas concentration be unknown at the same time when using such sensor units. When relying on such sensor units in breathing apparatuses, the system can therefore not distinguish changes in concentrations from changes in flow. Thus, there is a need to provide alternatives avoiding the aforementioned issues and it would for instance be advantageous to be able to measure flow and/or concentration independently.

Hence, an improved or alternative system for determining the presence of a substance delivered into a gas flow would be advantageous.

Hence, an improved breathing apparatus would be advantageous and in particular allowing for increased cost-effectiveness, improved reliability, versatility, and/or patients safety would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a breathing apparatus, a method, and a computer program according to the appended patent claims.

According to one aspect of the invention, a breathing apparatus is provided. The breathing apparatus has at least one delivery device for adding a volume of a substance to a gas flow. The delivery device has in some embodiments a gas inlet, and a gas outlet. The delivery device enriches a gas flow with a substance, adding a substance volume, preferably in gas form or in a gasifying form (e.g. injection of a liquid substance evaporating in the gas flow) to the gas flow. The apparatus further comprises a unit for monitoring a presence of the substance in a gas downstream the delivery device. The monitoring unit comprises a first sensor unit arranged at a first gas conduit at the gas outlet or downstream thereof. The first sensor unit is adapted to provide a first measurement value based on at least an acoustic property, such as a sound velocity related property, of a gas present in the first gas conduit. The apparatus further comprises a control unit operatively connected to the first sensor unit, wherein the control unit is arranged to determine the presence of the substance based on the first measurement value.

With the presence of the substance detected, embodiments implement the detection of the substance, or a concentration thereof for ensuring the safety of the breathing apparatus. A too low or too high concentration may be undesired. Alternatively, a non-delivery of a substance may be undesired and needs to be monitored. Suitable action may be initiated upon detection of an erroneous or non-desired function. For instance, a user may be informed of the potential malfunction. Alternatively, or in addition, the delivery device may be shut down or bypassed in order to cut off delivery of the substance.

According to another aspect of the invention, a method is provided. The method is a method of internally controlling a breathing apparatus. The method comprises the step of monitoring a presence of at least one substance in a gas downstream a delivery device added to a gas flow, wherein the monitoring comprises providing a first measurement value based on at least an acoustic property, such as a sound velocity related property, of a gas present in a first gas conduit by means of a first sensor unit arranged at the first gas conduit at a gas outlet of the delivery device or downstream thereof, and determining the presence of the substance based on the first measurement value.

According to yet another aspect of the invention a computer program is provided. The computer program is storable on a computer readable medium, for processing by a computer. The computer program comprises code segments for monitoring a presence of at least one substance in a gas downstream a delivery device added to a gas flow. The monitoring code segments comprise code segments for providing a first measurement value based on at least an acoustic property, such as a sound velocity related property, of a gas present in a first gas conduit by means of a first sensor unit arranged at the first gas conduit at a gas outlet of the delivery device or downstream thereof, and determining the presence of the substance based on the first measurement value.

Some embodiments provide for detecting a presence of a desired substance in a gas flow in a breathing apparatus.

Some embodiments provide for a detection of a concentration of a desired substance in a gas flow in a breathing apparatus.

Some embodiments provide for a detection of a too low or too high concentration of a desired substance in a gas flow in a breathing apparatus.

Some embodiments provide for control of a function of a delivery unit delivering the desired substance.

Some embodiments provide for suitable action to be initiated or taken upon detection of an erroneous or non-desired function of the delivery device.

Some embodiments of the invention provide for an independent measurement of a concentration of a certain gas or substance in a gas mixture and gas flow thereof independently.

Some embodiments provide for such independent measurements at a low cost thanks to a simple, but still accurate, sensor unit design.

Some embodiments provide for such measurement while avoiding a pressure drop in the conduit in which the measured gas flows.

Some embodiments avoid exerting an influence of the gas flow at all, as for instance no gas turbulence is caused in the conduit, or a mainstream measurement is provided without the need for a sample of gas taken from the flow.

Some embodiments provide for real time measurements without time delay, which is advantageous as steps can be taken faster than previously or even immediately for counter acting any faulty conditions detected.

Embodiments provide for main stream measurements avoiding any side stream related issues, such as where to dispose or feedback a sample gas volume after measurement.

Embodiments provide for measurements of the gas over the entire cross section of the conduit in which the measured gas is present.

Some embodiments provide for a compact sensor unit providing both a gas concentration measurement and a gas flow measurement, which is advantageous as the total gas delivery is monitored.

Some embodiments provide for fast measurements without having to analyze multiple properties of a gas mixture with advanced gas analyzers.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

FIGS. 1A and 1B are schematic illustrations of a combination of a delivery device and a monitoring unit.

FIGS. 2-4 and 8, respectively, are schematic illustrations of breathing apparatuses having embodiments of a delivery device and a monitoring unit.

FIG. 6 is a flowchart illustrating an embodiment of the method according to the invention.

FIG. 8 is a schematic illustration of a further embodiment of the invention.

DESCRIPTION OF THE PREFERRED EMBODIMENTS

Figure 3:
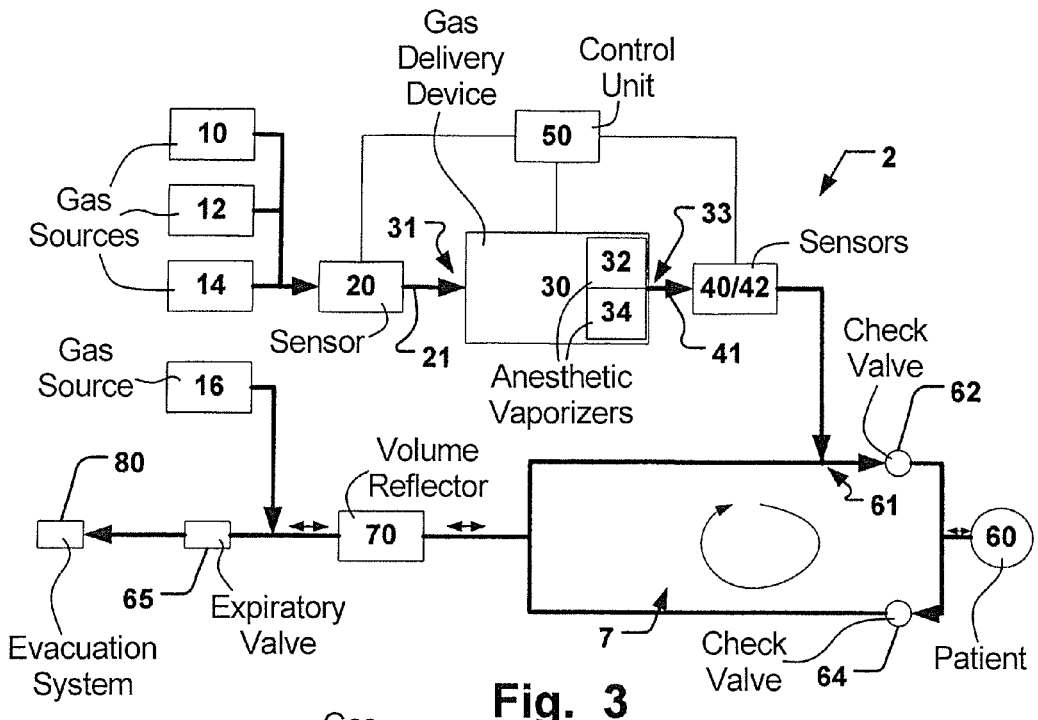

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to an anesthesia machine and in particular to some embodiments an anesthesia machine having a circle system. However, it will be appreciated that the invention is not limited to this application but may in some examples or embodiments be applied to many other breathing apparatuses, including for example intensive care ventilators with added anesthesia capabilities, ventilators with nebulizers for medicaments, and humidifiers in applications where dose control is critical, etc.

In FIG. 1A, a schematic illustration of a combination of a delivery device and a monitoring unit is shown. The delivery device is arranged for adding a volume of a substance to a gas flow. The substance is provided in gas phase in some embodiments. Alternatively, the substance may be provided in liquid form and injected into the gas flow, where it gasifies. In some embodiments, the substance may not be entirely gasified at the measurement location. In some embodiments, the substance may be provided in solid particle form, which is delivered to the gas flow. In all embodiments the substance changes the acoustic properties of the gas or gas mixture at the measurement location. The illustrated delivery device 30 has a gas inlet 31 and a gas outlet 33.

A unit for monitoring a presence of the substance in a gas downstream the delivery device 30 has a first sensor unit 40 arranged at a first gas conduit 41 at the gas outlet 33 or downstream thereof. The first sensor unit 40 is adapted to provide a first measurement value based on at least an acoustic property, such as a sound velocity related property, of a gas present in the first gas conduit 41. The aggregate further has a control unit 50 operatively connected to the first sensor unit 40, and arranged to determine the presence of the substance based on the first measurement value.

The monitoring unit may further include a second sensor unit 20 arranged at a second gas conduit 21 at the gas inlet 31 (FIG. 1A) or upstream thereof (FIG. 1B), adapted to provide a second measurement value based on at least an acoustic property, such as a sound velocity related property, of a gas present in the second conduit 21.

The gas present in the second conduit 21 is to be enriched with the substance by the delivery device 30, and then present in the first conduit 41. The gas either passes the delivery device for enrichment with the substance, as illustrated in FIG. 1A, or the substance is added to the gas on the passage from the second sensor unit 20 to the first sensor unit 40. The added substance will thus be present in the gas phase at the first sensor unit 40 in some embodiments.

The second sensor unit 20 may be omitted in some embodiments, as will be seen below, depending on the type of the first sensor unit 40. The second sensor unit 20 may be omitted in case the added gas flow volume and composition thereof is known in the system. Such data may be provided from other units in the system. An example is given below. However, for the sake of simpler illustration, focus is given to describing embodiments with a second sensor herein.

By having a first sensor unit 40 located at or in the vicinity of the outlet 33 of the delivery device 30, the function of the delivery device 30 can be monitored and controlled in the fastest possible way. This advantage can also be achieved by having a second sensor unit 20 at or in the vicinity of the inlet 31 of the delivery device 30, as the measurement values of the first and second sensor units may be compared as explained below. This is of critical importance for applications with injection-based delivery of the anesthetic agent in the main stream, as large doses could be delivered quickly, but could also be useful for other types of dose delivery devices and other means for dose delivery via patient gas.

If a deviation is detected in the delivered concentration of a substance, the control unit 50 may immediately correct the delivered dose by means of a regulatory loop, and alternatively, or in addition activate suitable measures such as alerting the user, or shut down or bypass the dose delivery device 30 (not shown) if the detected concentration is a potential patient hazard.

With traditional vaporizers operating with a bypass principle for dose delivery such large deviations in dose concentration cannot occur in case of an eventual error. Hence, the requirements on speed of monitoring and regulation do not exist in the same manner as described above. Therefore, the traditional way of monitoring dose concentrations is based on side stream measurements in other parts of the system and not direct vicinity of the dose delivery device as discussed previously.

In the case two sensor units are used, the composition and quantity of the gas flow delivered to the delivery device may also be monitored. Also in this case, deviations in gas composition may be corrected by a regulatory loop, and a user may be alerted if deviations from set values are detected.

The control unit 50 may be adapted to detect deviations from desired concentrations of the substance at the gas outlet 33 based on knowledge of the composition of the gas flow to the delivery device at the gas inlet 31. A very fast monitoring and regulation is thus provided. The concentration of a substance may be measured indirectly by measuring the change in acoustic properties of the gas. There is accordingly no need for specialized gas sensors, and a plurality of different gas mixtures may be monitored.

Hence, the control unit 50 may be adapted to detect deviations based on a change in an acoustic property of the gas in a first measurement value, obtained by a first sensor unit 40, i.e. actual delivered value, from an acoustic property value associated with the gas having the desired concentration of the substance. In this case, the acoustic properties of the gas having the desired concentration of the substance may be calculated by the control unit 50, as the expected acoustic properties. The actual acoustic properties of the gas at the gas outlet 33 may accordingly be compared with the expected acoustic properties of the gas, for fast regulation and monitoring without the need for specialized gas sensors for each gas in the mixture. The control unit 50 may be adapted to calculate an expected acoustic property of the gas at the gas outlet from knowledge of the gas at the gas inlet 31, such as a flow measurement value, and/or a composition measurement of the gas at the gas inlet, and/or a volume added by the delivery device 30, where the volume have an acoustic property, which can be determined by the control unit 50. The flow measurement value and composition measurement value of the gas at the gas inlet may be obtained by integrated sensors in the gas sources 10, 12, 14, or by a second sensor 20.

The control unit 50 may then be arranged to detect a deviation of an acoustic property of the gas at the gas outlet 33, as obtained by the first measurement value, from the expected acoustic property calculated by the control unit 50. Knowledge about a deviation from the calculated expected acoustic properties may then be used to determine if the delivery device 30 is functioning properly, and moreover regulate the gas flow and/or concentration by a regulatory loop.

A more detailed description of the embodiments follows below.

In embodiments, such as described with reference to FIGS. 1-4 and 8, both the first sensor unit 40 and the second sensor unit 20 are time of flight/sound velocity measurement units, such as schematically illustrated implementations by sensors 42, 43 or sensor 44 in FIGS. 5A, 5B and 5C that are described in more detail below.

The speed of sound through a gas mixture is different through different composed gas mixtures. When a substance is added, this generally alters the acoustic properties of the gas mixture. The speed of sound is then different with or without the substance. This principle can be used as a basis to detect the presence or absence of a substance in a gas or gas mixture. Moreover, a measurement of a concentration of said substance in the gas or gas mixture may be determined, e.g. based on a look-up table. Temperature compensation may be provided as described below.

Alternatively, or in addition, a comparison of measurements of the same gas or gas mixture without the substance added and with the substance added may be made for determining the presence of the substance or concentration thereof at the first sensor unit. Temperature compensation may be provided as described below.

Formula (1) represents the speed of sound c in a gas or mixture of gases as:

$$c = \sqrt{\frac{C_p}{C_v} \frac{R \cdot T}{M}} \quad (1)$$

wherein
c is the speed of sound [m/s]
$C_p$ is the specific heat at constant pressure [J/mol K]
$C_v$ is the specific heat at constant volume [J/mol K]
R is the ideal gas constant=8.3143[J/mol K]
T is the absolute temperature [K]
M is the molecular weight [kg/mol]

For a given ideal gas the speed of sound c depends only on its temperature. At a constant temperature, the ideal gas pressure has no effect on the speed of sound, because pressure and density, which is also proportional to pressure, have equal but opposite effects on the speed of sound, and the two contributions cancel out exactly.

As the temperature in conduits in breathing apparatus may vary, a temperature compensation may be provided to ensure a correct measurement of the sound of speed.

The speed of sound in gas can be detected by sending a sound pulse through the gas and measuring the transit time of the sound pulse through the conduit in which the gas is located, called the time of flight (TOF) for a sound pulse through the gas or gas mixture. As shown in FIGS. 5A-5C, the sound pulse is generated by a first transducer T1 and sent towards a second transducer T2 receiving the pulse. The transducer may be piezo crystal based transducers.

Examples for the speed of sound through various gases are given in table 1 below.

TABLE 1 approximate speed of sound of pure gases at 25° C., i.e. 298 K

| Gas/vapor | c [m/s] |
|---|---|
| Air | 346 |
| Oxygen—$O_2$ | 329 |
| Nitrous oxide—$N_2O$ | 268 |
| Desflurane | 127 |

The measured value by the first or second sensor unit 40, 20 is thus the TOF of a sound pulse through the gas in a conduit at the location of the sensor unit 40, 20. A change in the mixture of the gas causes a change in TOF.

Since substance concentration has a substantial influence on the speed of sound of the gas mixture, there is a great difference in the time of flight between the sound pulses traversing a gas mixture with the substance and the sound pulses traversing an equal distance in the gas mixture without the substance. As can be seen from table 1, anesthetic agents, given as an example in table 1, differ considerably in sound speed from other fresh gas components (fresh gas is here the gas to be enriched with the substance, e.g. present at the second sensor unit 20). This allows for a very accurate measurement of the concentration of anesthetic agents in fresh gas, based on measurements of the acoustic properties of such gas mixtures.

For instance, a substance concentration added by the delivery device 30 in the gas can be determined and used by the control unit 50.

The control unit 50 may determine the change in TOF and control unit 50 thus determines that a substance is present based on such a relative change of TOF over time.

Moreover, the degree of change in TOF may be used by control unit 50 to establish the concentration in the gas mixture, based on changes in the acoustic properties by the added substance.

For instance, when the amount or concentration of fresh gas components of air, oxygen and/or nitrous oxide delivered by the gas sources 10, 12, 14 before adding the anesthetic agent are known in a breathing apparatus (see e.g. in the embodiment described below with reference to FIG. 4), the concentration of the anesthetic agent added by a vaporizer is effectively determinable by sensor units measuring the sound of speed of the gas composition. Even when the amount or concentration fresh gas components of air, oxygen and/or nitrous oxide delivered by the gas sources 10, 12, 14 before adding the anesthetic agent is not known (see e.g. in the embodiments described below with reference to FIGS. 2 and 3), some embodiments still provide an effective and accurate measurement of the anesthetic agent concentration. In the latter case a second sensor unit 20 based on acoustic measurement principles is arranged at a conduit before addition of the anesthetic agent is made. The two point measurement allows for differential determination of the concentration of the added anesthetic agent.

Knowledge of the type of substance or anesthetic agent may be used in order for the control unit 50 to use the TOF measurement to determine the concentration of the substance or anesthetic agent.

Figure 5A:
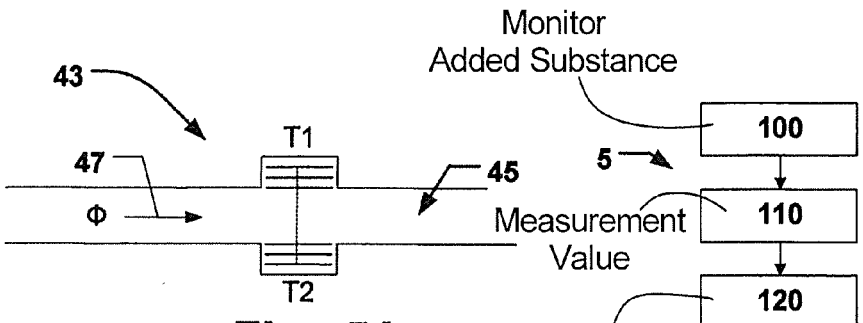
FIGS. 5A-5C, respectively are schematic illustrations of three ultrasonic sensor units.
Figure 5B:
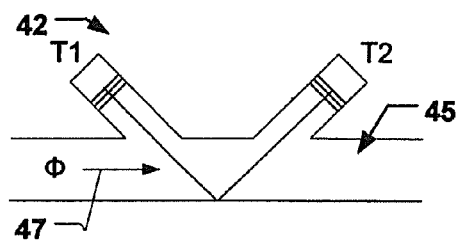
Figure 5C:
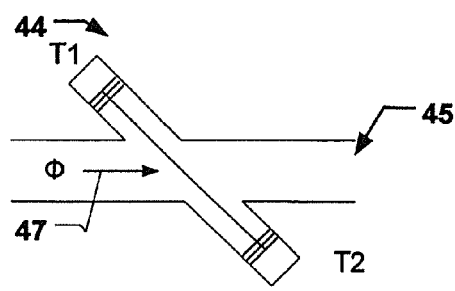

FIGS. 5A, 5B, and 5C show three exemplary geometries and principles of a gas component concentration measurement sensor unit or gas component identification sensor unit using e.g. an ultrasound transceiver which measures the time of flight (TOF) for a sound pulse passing through the gas to be identified. An ultrasonic measurement sensor 42 of the type as illustrated in FIG. 5B, i.e. sending sound pulses at an oblique angle in relation to the gas flow direction, such that pulses travel along or against the gas flow in one of the two directions. An ultrasonic measurement sensor 43 of the type as illustrated in FIG. 5A, i.e. sending sound pulses in a direction substantially perpendicular to the gas flow direction. FIG. 5C shows a further embodiment of an ultrasonic measurement sensor 44, sending sound pulses at an oblique angle in relation to the gas flow direction. By having the transducers T1 and T2 of the sensor 44 in the configuration as shown in FIG. 5c the distance between the transducers is reduced, compared to FIG. 5b. This may be advantageous in case detecting gases with a high acoustic dampening. The transducers of the sensors may be piezo crystal based transducers, which allow for both sending and receiving sound pulses.

Sensor units 20 and 40 may be implemented as ultrasonic measurement sensors 42, 43 as shown in FIGS. 5A, 5B, and 5C.

An ultrasonic measurement sensor 42 of the type as illustrated in FIG. 5B, i.e. sending sound pulses at an oblique angle in relation to the gas flow direction, may provide one or more of the following measurement values:

1. The gas flow $\phi$ in a conduit 45 by measuring the difference in TOF upstream and downstream relative the gas flow:

Gas flow $\phi = k^*(Tu-Td)/(Tu^*Td)$, wherein

Tu=propagation time for an upstream sound pulse (against the gas flow direction 47), Td=propagation time for a downstream sound pulse (in the gas flow direction 47), and k is a constant that depends on the geometrical properties of the flow duct and the position of the transducers.

2. The speed of sound c $c = L^*2/(Tu+Td)$, wherein

L is the distance between the transducers.

The speed of sound c provides for calculation of the molecular weight M of the gas in the conduit 45 according to formula (1), when compensated for gas temperature. Gas temperature is for instance measured with a separate temperature sensor, or may be based on temperature measurements made in the breathing apparatus for other purposes.

3. Attenuation of the sound pulse, i.e. decrease of sound pulse amplitude when travelling through the gas in conduit 45. Different gases let pass a different amount of sound energy. Attenuation is determined from the amplitude of the detected pulse that has travelled through the gas.

Monitoring of the function of one or more dosage units or a gas delivery unit providing the fresh gas to be enriched with the substance delivered by the delivery unit may then be based on at least one of the follow entities, alone or in combination:

1. A difference in gas flow $\phi$ before and after enriching the fresh gas with the substance. An increase in gas flow when comparing a flow measurement between units 20 and 40 indicates that molecules of the substance have been added to the fresh gas flow by delivery unit 30, see FIG. 1:

$\phi_1 > \phi_2$

Temperature of the gas travelling from the second sensor unit 20 to the first sensor unit 40 may change on the passage, e.g. in the delivery device. In case the gas temperature is different at the location of the first unit 40 and the second unit 20, temperature compensation of the gas flow may be made based on local temperature measurements at the respective location in order to achieve accurate measurements.

2. A difference in sound velocity c of the gas mixture (compensated for temperature at 20 and 40 respectively) between the sensor units 20, 40, i.e. $c_2 \neq c_1$, then the molecular weight M has changed between sensor unit 20 and sensor unit 40:

$M_1 \neq M_2$

This change in molecular weight is due to the substance added to the fresh gas flow by delivery unit 30.

When adding one or more anesthetic agents, which have a much higher molecular weight than air, oxygen, or nitrous oxide (see table 1), then $M_1 > M_2$ as measured or determined $c_2 > c_1$ In case the gas temperature is different at the location of the first unit 40 and the second unit 20, temperature compensation of the gas flow may be made based on local temperature measurements at the respective location.

3. A difference in attenuation measured at the first sensor unit from that attenuation measured at the second sensor unit, is indicative of a substance added in gas phase by delivery unit 30 to the fresh gas flow.

Considering the above, the following can be applied:

a. The second sensor unit 20 may be omitted in certain embodiments—in case the composition of the fresh gas mixture and/or the gas flow at the position of the second sensor unit 20 is known. In certain breathing apparatuses, the composition of the gas mixture or the gas flow may be known, e.g. from an already existing measurement, sensor, flow regulator, etc. E.g. the values set for gas flow and gas composition to be delivered at inlet 21 may be used for calculations and measurements according to the invention. A second sensor 20 may be advantageous for monitoring the delivered gas mixture in case gas composition and/or concentration is uncertain. A concentration of certain gases in the gas mixture allows for a calculation of the molecular weight M of the gas mixture components respectively.

b. There is no need to determine or measure the entire range of the above parameters 1.-3. For instance, if only sound of speed and attenuation are determined, a more simple and compact sensor unit configuration measuring perpendicular to the gas flow is sufficient, as illustrated in FIG. 5A.

A plurality of sound pulses may be generated in a series by the actuating transducer of the sensor units. Signal parameters like pulse edge, pulse shape, frequency, number of pulses etc. are adapted to the specific characteristics of the transducer. Alternatively, a continuous signal, such as a sine wave, may be provided to actuate the transmitting transducer. By measuring a phase difference between the sent signal and the signal received by the receiving transducer, the influence of the gas on the sound signal is detectable and a measurement value similar useable as TOF explained herein.

Now turning to FIGS. 2-4, some specific embodiments of breathing apparatuses implementing various of the above described aggregates are described hereinafter.

In some embodiments, the first sensor unit is an ultrasonic flow meter based on bidirectional velocity of sound measurements, as illustrated in FIGS. 5B-C and explained with reference thereto.

As shown in FIGS. 1A and 1B, the control unit 50 is operatively connected to the second sensor unit 20, and arranged to determine the presence of the substance based on a comparison of the first measurement value and the second measurement value. The second sensor unit 20 may be omitted as described above, and as shown in FIG. 4.

The control unit 50 of embodiments may be connected to further control units of the breathing apparatus, e.g. for taking appropriate action upon detection of non-desired substance presence or concentration thereof.

The first sensor unit 40 and the second sensor unit 20 are in embodiments of the same type and the comparison of the first measurement value and the second measurement value is based on a difference in measurement signals thereof. The difference is a measure for a concentration of the substance in the gas in the first conduit 41, delivered by the delivery unit 30.

The control unit 50 is in this embodiment, and may be so also in other embodiments, arranged to compensate for a time delay of a gas when flowing between the first sensor unit 40 and the second sensor unit 20. The gas may flow in a single mainstream configuration between the two sensor units 20, 40, for instance through the delivery device, as shown in FIG. 1A. Alternatively, the gas may flow in a mainstream and one or more sidestream between the two sensor units 20, 40. The gas flow passing the second sensor unit 20 may even reach the first sensor unit 40 without passing through the delivery device 30. In the latter case, the substance may be added as such, without a carrier gas, to the gas flow between the two sensor units 20, 40. Substances may for instance be added in a configuration, as shown in FIG. 1B, e.g. based on a substance injector principle.

The time delay of the gas flow between two sensor units 20, 40 may be chosen in dependence of a gas flow rate of the gas when flowing between the first sensor unit 40 and the second sensor unit 20.

The time delay (t2−t1) is suitably chosen such that the control unit 50 provides a measure or data based on the comparison of the same gas travelling between the second and first sensor unit. This may be based on two different time, when the gas is at a first time t1 at the position of the second gas sensor 20 (without the substance added), and when the gas has reached the first sensor unit 40 at a later time t2 (with the substance added).

The first sensor unit may be an ultrasonic flow sensor 42 devised to provide a flow measurement value and a concentration measurement of the substance. An ultrasonic flow sensor 42 is schematically illustrated in FIG. 5B.

The control unit 50 is arranged to determine one or more of a quantity of the substance added, a volume of the substance added, or a concentration of the substance added.

The first and/or second sensor units are devised to substantially not interfere with gas flow in the conduit when passing the sensor unit. A turbulence, pressure drop, a time delay necessary for the measurement, a sidestream flow taken from the main stream, an interaction changing the chemical composition of the substance, etc. are avoided. Compensation, e.g. necessary for a pressure drop at the measurement location is not needed.

Alternative delivery devices may be arranged in other configurations, e.g. as an injector device injecting the substance into a gas stream, such as illustrated in FIG. 1B. In this case, the delivery device 30 does not need a gas inlet. Delivery of the substance may be accomplished by a pressurized delivery of the substance into a gas flow in a main conduit at a delivery point 35. The substance may be directly injected into the main conduit, or be delivered with a gas flow from a side stream delivered into the main stream at a delivery point 35. In the latter case only, the delivery device has a gas inlet 31, which may be supplied with gas from a branching second conduit 21.

In an embodiment of the invention according to FIG. 2, a breathing apparatus 1 is shown. Fresh gas to be entered into a circle system is delivered by controllable fresh gas sources, such as a first gas source for air 10, a second gas source 12 for oxygen, and a third gas source for nitrous oxide 14. A desired mixture of these gases may be chosen by a user of the apparatus 1 or automatically adjusted in dependence of user settings and other conditions in the breathing circuit, in a known manner.

The fresh gas is passing a first sensor unit 20 towards the delivery unit 30. The delivery unit 30 of the embodiment comprises a first anesthetic vaporizer 32 and a second anesthetic vaporizer 34. The first anesthetic vaporizer 32 is arranged to deliver a first anesthetic agent, and the second anesthetic vaporizer 34 is arranged to deliver a second anesthetic agent. Usually only one of the two vaporizers 32, 34 is in operation in order to avoid mixtures of the two anesthetic agents. Other embodiments may have only a single delivery unit or anesthetic vaporizer. The vaporizers 32, 34, may each have an associated sensor unit 40 (not shown), i.e. a first sensor unit 40 at outlet of the vaporizer 32, and a first sensor unit 40 at outlet of the vaporizer 34. In this may rapid detection, monitoring, or control of each of the vaporizers 32, 34 may be obtained, as elucidated previously and below. Likewise, a second sensor 20 may associated with each of the vaporizers 32, 34, but a single sensor 20 may be sufficient if a single gas is input to the vaporizers 32, 34.

The gasified anesthetic agent enters the circle system in a fresh gas mixture at entry point 61. Inspiratory check valve 62 and expiratory check valve 64 ensure the flow direction in the circle system 7. Expiratory valve 65 is closed during inspiration and controls a release from the circle system, e.g. to an evacuation system 80 or similar during expiration. A volume reflector 70 may be present in the system. The volume reflector 70 may ensure refilling of the circle system with gas during inspiration, as provided by a controllable gas source 16, usually of an oxygen gas source. Alternatively, a bellow (not shown) is used for circulation of the gas. A ratio of rebreathing is suitable adjusted by a control unit of the breathing apparatus 1, which might be the control unit 50 or a separate control unit. The ratio of rebreathing is adjusted by suitably controlling fresh gas sources 10-12 and gas source 16 for the reflector during inspiration.

The anesthetic vaporizers 32, 34 have a reservoir for the liquid anesthetic agent from which the volume of the anesthetic agent is added to the fresh gas flow in a suitable manner, wherein the gas flow enters the delivery device at the gas inlet and leaves the delivery device with the substance added to the gas stream at the gas outlet. The gas outlet of the delivery device is in fluid communication with a first gas outlet of the apparatus to which a patient 60 is connected during certain operation of the apparatus.

The anesthetic vaporizers 32, 34 are anesthetic delivery devices as known in the art, including one of an injection vaporizer, or an evaporation vaporizer, for adding the volatile liquid anesthetic agent in gasified form to the fresh gas flow. The vaporized anesthetic agent adds an extra gas flow to the fresh gas flow.

A presence of the anesthetic agent in the gas downstream the delivery device 30 is measured as follows. The first sensor unit 40 is arranged at the first gas conduit 41 at the gas outlet 33 or downstream thereof.

The second sensor unit 20, if provided, is in some embodiments an ultrasonic sound velocity sensor to provide a second TOF measurement value of the fresh gas provided by fresh gas sources 10, 12, 14 present in the first gas conduit (41). The gas has a known composition, e.g. a known oxygen content and/or nitrous oxide content adjusted by the fresh gas sources 10, 12, 14. The gas at the first sensor unit 40 will have the same composition with regard to these components as it is carried to the first sensor unit 40. It will be understood that the second measurement value will be provided first in time and the first measurement value subsequently when the gas has travelled along the gas conduits to the first sensor 40.

The first sensor unit 40 is an ultrasonic sound velocity sensor to provide a first TOF measurement value of the gas in the conduit 41, which is enriched with a flow of gasified anesthetic agent.

The control unit 50, operatively connected to the first sensor unit 40 and the second sensor unit 20, determines the presence of the anesthetic agent as described above by differential measurement, preferably with the aforementioned time delay compensation for the travel of gas between the measurement points.

The first sensor unit 40 is located at or in the vicinity of the outlet of the delivery unit. This allows for a quick detection of the presence of the anesthetic agent. As previously mentioned this is of critical importance for applications with injection-based delivery of the anesthetic agent in the main stream, as large doses could be delivered quickly.

In this manner, the control unit 50 is adapted to detect an error, deviation, or faulty function in the delivery unit 30 or at least one of fresh gas sources 10-14 arranged to provide the fresh gas flow to the gas inlet. This may be based on a detection of a deviation from a desired concentration of the anesthetic agent. The desired concentration of the anesthetic agent may be based on a user input via a suitable user interface of the breathing apparatus 1. Alternatively, or in addition, the detection of a deviation may be based on a detection of any substance delivered by the delivery unit 30. In the latter case, the control unit may be set to expect a delivery of a detectable amount of the substance by the delivery unit 30. In the case, no delivery of a substance is detected, suitable action may be activated or taken. This may be implemented by having both a first sensor unit 40 and a second sensor unit 20, and detecting a difference in the measurement signal of the both sensor units.

Upon detection of erroneous values, the control unit 50 may alert the user suitably. Alternatively, or in addition, suitable measures may be taken in the apparatus 1, e.g. shut down/blocking the delivery unit or activation of a gas flow bypass conduit for bypassing the delivery unit 30 with fresh gas upon detection of a concentration of the substance that is higher than a desired concentration. Alternatively, or in addition, the dose of anesthetic agent may be adjusted immediately to the desired value by a regulatory loop.

The control unit 50 may be adapted to detect aforementioned deviation based on a change in an acoustic property of the gas at the gas outlet 33, as provided by the first measurement value, from an acoustic property value associated with the gas having the desired concentration of the substance. Hence, a faulty function of the control unit may be detected by comparing the actual acoustic properties of the gas at the gas outlet 33 with the expected acoustic properties of the gas having the desired composition and/or gas flow.

The control unit 50 may be adapted to determine an expected acoustic property of the gas at the gas outlet 33 from a flow measurement value and/or a concentration measurement of the substance of the gas at the gas inlet 31. The control unit 50 may be provided with data about the gas composition and/or gas flow of the gas before passing the delivery device 30, and data about the desired concentration of the substance in the gas at the gas outlet 33, and thereafter calculate the expected acoustic properties of the gas at the gas outlet 33 based on aforementioned data, which data may be provided by an integrated sensor unit in the gas sources 10-14 or by a second sensor unit 20. Subsequently, the control unit 50 may be arranged to detect a faulty function in the delivery device

30 by detection of a deviation of an acoustic property of the gas at the gas outlet 33, as provided by the first measurement value, from the calculated expected acoustic property at the gas outlet 33.

In all embodiments, the possibility to generate an alarm if the measurement values indicate that the identified gas composition deviates from the gas composition the user has chosen, or if no gas is identified, increases the overall safety of the breathing apparatus. A display on the user interface facilitates the understanding of what is going on in the system.

A further breathing apparatus 2 having an embodiment of the invention is illustrated in FIG. 3. Similar elements are shown as in the embodiment of FIG. 2. However, the first sensor unit is an ultrasonic flow sensor 42 of the specific type as shown in FIG. 5B.

The flow sensor 42, as shown in FIG. 5B, is primarily arranged to measure gas flow. The transit time for sound pulses Tu respectively Td are measured, as explained above. The flow is equal to k1*(Tu−Td)/(Tu*Td). Secondly, the TOF is determined from that mean value of Tu and Td, (Tu+Td)/2, as the sound of speed is inversely proportional to the TOF. In case the speed of sound c and the temperature T at the measurement location of the sensor unit are known, the admixture of a specific gas into a known gas mixture can be determined.

Figure 4:
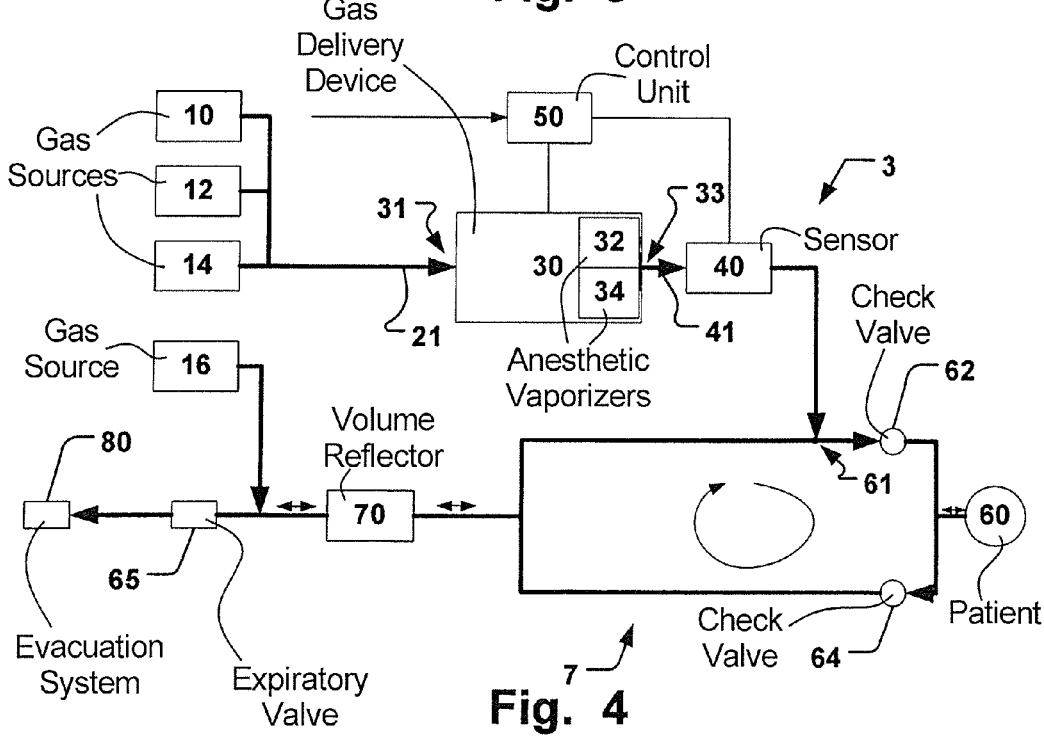

In another breathing apparatus 3 implementing an embodiment of the invention according to FIG. 4, similar elements are shown as in the embodiment of FIG. 3. However, the second sensor unit 20 is omitted. This is an embodiment where the gas concentrations of components of a gas mixture is known at the inlet of the second sensor unit 20, and it is sufficient to only measure the conditions at the first sensor unit 40. The effect that a supply of a gaseous substance by delivery unit 30 has on e.g. speed of sound or sound attenuation, is sufficient to provide the above calculations. This could for instance be the case if a single gas is connected to the inlet of the second sensor unit 20, or if air is connected to the inlet of the second sensor unit 20. A good gas mixer can give the same conditions and provide the gas concentrations to the calculation unit 50, as indicated in FIG. 4 by the dotted line entering the control unit 50 from the direction of the gas sources 10-14.

If the flow is known at the inlet of the second sensor unit 20, the flow added from the delivery unit 30 is calculated by subtracting the flow value at the inlet of 20 (unit 20 is non-existent or passive) from the measured flow at the first sensor unit 40. The second sensor unit 20 may thus be omitted.

Figure 8:
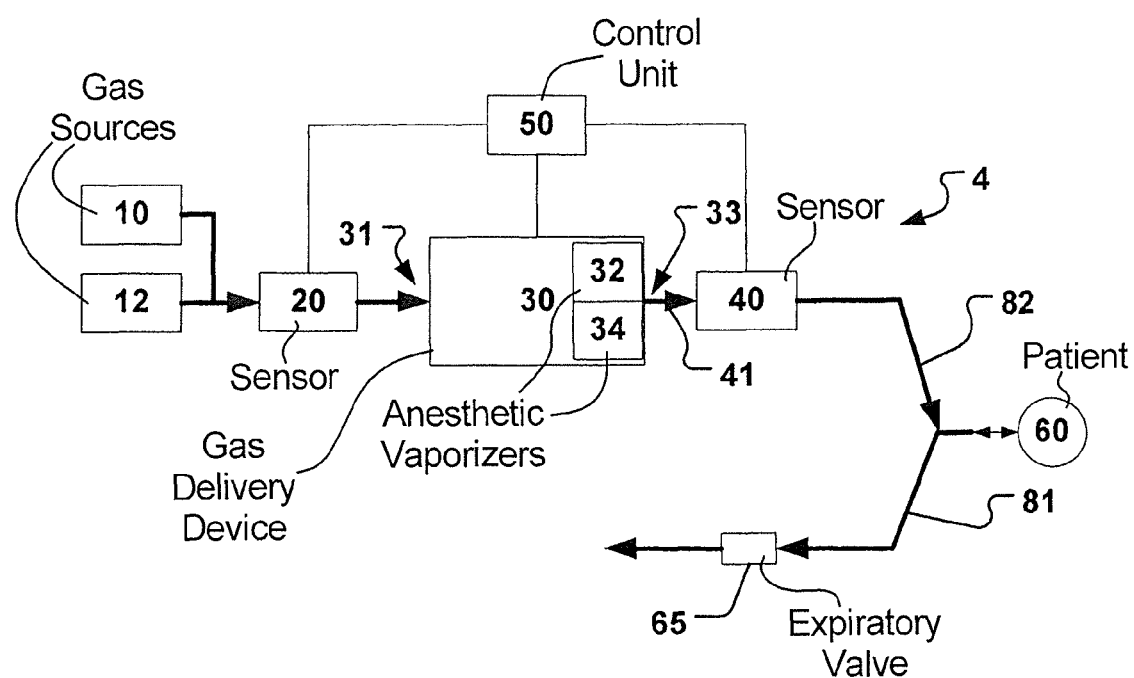

A further breathing apparatus 4 having an embodiment of the invention is illustrated in FIG. 8. Similar elements as in the embodiment of FIG. 2 have the same reference numerals. The apparatus 4 is for instance an open system anesthesia machine, i.e. without a circle system for re-using exhaled gases during subsequent inhalations, or an intensive care ventilator, where exhaled gases are disposed after exhalation. A substance is added to the gas flow in inspiratory line 82 and delivered to the patient 60 during the inspiratory phase of a breathing cycle. During the subsequent expiratory phase exhalation gases from the patient 60 are led via expiration line 81 and the expiratory valve 65 from the breathing apparatus 4.

The substance may be added by the delivery device 30 to an intermittent gas flow or a continuous gas flow. The measurement unit of embodiments of the invention is adapted to provide the aforementioned measurements both for intermittent delivery and continuous delivery.

An intermittent delivery may occur in embodiments of the type described with reference to FIGS. 2-4 as fresh gas may only be delivered to the breathing circuit during an inspiratory phase and/or when re-filling the breathing circuit with fresh gas, depending on the mode of operation of the breathing apparatus 1-3.

An intermittent delivery may occur in embodiments of the type described with reference to FIG. 8, or for instance in a breathing circuit according to WO2010081914, as inspiratory gas may only be delivered to the patient during an inspiratory phase. In addition, a continuous bypass flow may be provided from the gas sources 10,12, passing the delivery device towards the expiratory valve, both during the inspiratory phase and the expiratory phase, e.g. in order to detect triggering of a new inspiratory phase by the patient via a gas flow trigger, which is known to the skilled person. In the latter case, the substance is delivered continuously, even though not the entire amount thereof is delivered to the patient 60 at all times.

During intermittent delivery, i.e. a temporary stop occurs in the gas flow to which the substance is added, either through the delivery device (see FIG. 1A) or in the main stream (see FIG. 1B). This stop time is taken into consideration when calculating the above described time delay for the gas passage from the second sensor unit 20 to the first sensor unit 40.

The measurements described above are also provided during continuous delivery of the substance.

FIG. 6 is flowchart illustrating a method 5 of internally controlling a breathing apparatus, such as the apparatuses 1, 2, 3, or 4 described above. The method 5 includes monitoring 100 a presence of at least one substance in a gas downstream a delivery device 30 added to a gas flow. The monitoring comprises providing 110 a first measurement value based on at least an acoustic property, such as a sound velocity related property, of a gas present in a first gas conduit 41 by means of a first sensor unit 40 arranged at the first gas conduit 41 at a gas outlet 33 of the delivery device 30 or downstream thereof, and determining 120 the presence of the substance based on the first measurement value.

Figure 7:
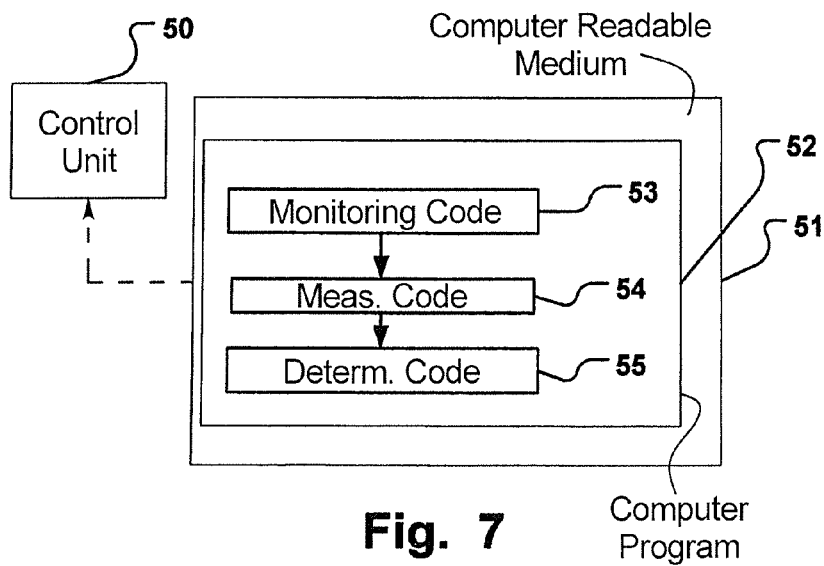
FIG. 7 is a schematic illustration of a computer program according to the invention.

FIG. 7 is a schematic illustration of a computer program 52 that is stored on a computer readable medium 51, for processing by a computer, such as the control unit 50. The computer program 52 comprises code segments for monitoring 53 a presence of at least one substance in a gas downstream a delivery device 30 added to a gas flow, wherein the monitoring comprises code segments for providing 54 a first measurement value based on at least an acoustic property, such as a sound velocity related property, of a gas present in a first gas conduit 41 by means of a first sensor unit 40 arranged at the first gas conduit 41 at a gas outlet 33 of the delivery device 30 or downstream thereof, and determining 55 the presence of the substance based on the first measurement value.

The present invention has been described above with reference to specific embodiments. However, other embodiments than the above described are equally possible within the scope of the invention. The delivery devices may in some embodiments for instance be a humidifier unit for adding water vapor, or a nebulizer unit for adding droplets of the substance to the gas stream. Different method steps than those described above, performing the method by hardware or software, may be provided within the scope of the invention. The different features and steps of the invention may be combined in other combinations than those described.

Although modifications and changes may be suggested by those skilled in the art, it is the intention of the inventors to embody within the patent warranted heron all changes and modifications as reasonably and properly come within the scope of their contribution to the art.

We claim as our invention:

1. A breathing apparatus comprising:
    at least one delivery device that adds a volume of a substance to a gas flow, said delivery device having a gas inlet and a gas outlet;
    a monitoring unit configured to monitor a presence of said substance in a gas downstream said delivery device;
    said monitoring unit comprising a first sensor unit arranged at a first gas conduit at said gas outlet or downstream thereof, said first sensor unit being configured to provide a first measurement value based on at least an acoustic property, such as a sound velocity related property, of a gas present in said first gas conduit;
    said monitoring unit comprising a second sensor unit arranged at a second gas conduit at said gas inlet or upstream thereof, configured to provide a second measurement value based on at least an acoustic property, such as a sound velocity related property, of a gas present in said second conduit; and
    said monitoring unit comprising a control unit operatively connected to said first sensor unit and said second sensor unit, and configured to determine said presence of said substance based on a comparison of said first measurement value and said second measurement value, said control unit being configured to compensate for a time delay of gas such that the first measurement value and the second measurement value are determined based on a same gas mass, when said gas is flowing between said first sensor unit and said second sensor unit through said delivery device, in said comparison of measurements.

2. The apparatus of claim 1, wherein said control unit is configured to detect a deviation in said delivery device, and/or a deviation from a desired concentration of said substance, based on knowledge of the desired composition of said gas flow to said delivery device at said gas inlet.

3. The apparatus of claim 2, wherein said control unit is configured to detect said deviation based on a change in an acoustic property of said gas in said first measurement value from an acoustic property value associated with said gas having said desired concentration of said substance.

4. The apparatus of claim 1, wherein said control unit is configured to calculate an expected acoustic property of said gas at said gas outlet from a flow measurement value of said gas upstream of said delivery device, and wherein said control unit is configured to detect a deviation of an acoustic property of said gas in said first measurement value from said expected acoustic property.

5. The apparatus of claim 1, wherein said first sensor unit is an ultrasonic sensor configured to provide a flow measurement value and/or a concentration measurement of said substance.

6. The apparatus of claim 1, wherein said first sensor unit is located at or in the vicinity of said gas outlet of said delivery unit.

7. The apparatus of claim 1, wherein said substance is a volatile anesthetic agent, and said delivery device is an anesthetic delivery device, including one of an injection vaporizer, or an evaporation vaporizer, for adding said volatile anesthetic agent to said gas flow.

8. The apparatus of claim 1, wherein said control unit is configured to detect an error in said delivery device or at least one gas source arranged to provide said gas flow to said gas inlet, by detection of a deviation from a desired concentration of said substance.

9. The apparatus of claim 8, wherein said control unit is configured to activate a gas flow bypass conduit for bypassing said delivery device, and/or shut down said delivery device upon detection of a concentration of said substance that is higher than a desired concentration.

10. The apparatus of claim 8, wherein said control unit is configured to activate an alarm for notification to a user upon detection of said error.

11. The apparatus of claim 8, wherein said control unit is configured to activate a regulatory loop for adjustment of said concentration of said substance to said desired concentration upon detection of said error.

12. The apparatus of claim 1, wherein said control unit is arranged to determine said presence of said substance based on a comparison of said first measurement value and a gas composition and a gas flow at said gas inlet.

13. The apparatus of claim 1, wherein said control unit is configured to determine one or more of a quantity of said substance added, a volume of said substance added, or a concentration of said substance added.

14. The apparatus of claim 1, wherein said first sensor unit and/or said second sensor unit are based on a measurement of a time of flight (TOF) for a sound pulse.

15. The apparatus of claim 1, wherein said second sensor unit is configured to directly measure a stream of said gas in said second gas conduit without sampling thereof.

16. The apparatus of claim 15, wherein said second sensor unit is an ultrasonic sensor configured to provide a measurement selected from the group consisting of flow measurement value and a concentration measurement of said substance.

17. The apparatus of claim 1, wherein said first sensor unit and said second sensor unit are of a same type and said comparison is based on a difference in measurement signals thereof, which difference is a measure for a concentration of said substance in said gas in said first conduit.

18. The apparatus of claim 1, wherein said time delay is chosen dependent on a gas flow rate of said gas when flowing between said first sensor unit and said second sensor unit.

19. A method of internally controlling a breathing apparatus comprising:
    monitoring a presence of at least one substance in a gas downstream a delivery device added to a gas flow;
    in said monitoring, providing a first measurement value based on at least an acoustic property, such as a sound velocity related property, of a gas present in a first gas conduit by operation of a first sensor unit arranged at said first gas conduit at a gas outlet of said delivery device or downstream thereof;
    in said monitoring, providing a second measurement value based on at least an acoustic property, such as a sound velocity related property, of said gas present in a second gas conduit by operation of a second sensor unit arranged at a second gas conduit at a gas inlet of said delivery device or upstream thereof;
    in said monitoring, compensating for a time delay of gas such that the first measurement value and the second measurement value are determined based on a same gas mass when flowing between said first sensor unit and said second sensor unit through said delivery device, and
    in said monitoring, determining said presence of said substance based on a comparison of said first measurement value and said second measurement value.

20. A non-transitory computer readable storage medium comprising code segments that, when said storage medium is loaded in a computer cause the computer to:
    monitor a presence of at least one substance in a gas downstream a delivery device added to a gas flow;
    implement the monitoring by providing a first measurement value based on at least an acoustic property, such as a sound velocity related property, of a gas present in a first gas conduit by operation of a first sensor unit arranged at said first gas conduit at a gas outlet of said delivery device or downstream thereof;

implement the monitoring by providing a second measurement value based on at least an acoustic property, such as a sound velocity related property, of said gas present in a second conduit by operation of a second sensor unit arranged at the second gas conduit at a gas inlet of said delivery device or upstream thereof;

implement the monitoring by compensating for a time delay of gas such that the first measurement value and the second measurement value are determined based on a same gas mass when flowing between said first sensor unit and said second sensor unit through said delivery device; and implement the monitoring by determining said presence of said substance based on a comparison of said first measurement value and said second measurement value.

21. The apparatus of claim 1 wherein said control unit is configured to calculate an expected acoustic property of said gas at said gas outlet from a composition measurement of said gas at said gas inlet, and wherein said control unit is configured to detect a deviation of an acoustic property of said gas in said first measurement value from said expected acoustic property.

22. The apparatus of claim 1 wherein said delivery device adds a volume, having an acoustic property, to said gas, and wherein said control unit is configured to calculate an expected acoustic property of said gas at said gas outlet from said acoustic property of said volume, and wherein said control unit is configured to detect a deviation of an acoustic property of said gas in said first measurement value from said expected acoustic property.

* * * * *